United States Patent
Ogusu

(10) Patent No.: US 8,257,664 B2
(45) Date of Patent: Sep. 4, 2012

(54) DISPENSING APPARATUS AND AUTOMATIC ANALYZER

(75) Inventor: Hiroyuki Ogusu, Shizuoka (JP)

(73) Assignee: Beckman Coulter, Inc., Brea, CA (US)

( * ) Notice: Subject to any disclaimer, the term of this patent is extended or adjusted under 35 U.S.C. 154(b) by 139 days.

(21) Appl. No.: 12/341,445

(22) Filed: Dec. 22, 2008

(65) Prior Publication Data

US 2009/0169434 A1 Jul. 2, 2009

Related U.S. Application Data

(63) Continuation of application No. PCT/JP2007/062313, filed on Jun. 19, 2007.

(30) Foreign Application Priority Data

Jun. 21, 2006 (JP) ................................. 2006-171609

(51) Int. Cl.
B01L 3/02 (2006.01)

(52) U.S. Cl. ...... 422/501; 422/509; 422/522; 73/864.11

(58) Field of Classification Search .................... 422/50, 422/82.13, 100, 67, 501, 509–526; 73/864.01–864.25

See application file for complete search history.

(56) References Cited

U.S. PATENT DOCUMENTS

| 5,499,545 A | 3/1996 | Kimura et al. | |
| 5,965,828 A * | 10/1999 | Merriam | 73/863 |
| 6,370,942 B1 * | 4/2002 | Dunfee et al. | 73/37 |
| 7,964,160 B2 * | 6/2011 | Zuppiger et al. | 422/500 |
| 8,147,773 B2 * | 4/2012 | Lemme et al. | 422/501 |

FOREIGN PATENT DOCUMENTS

| JP | H2-045818 | 12/1990 |
| JP | 7-5014 | 1/1995 |
| JP | 7-6995 B2 | 1/1995 |
| JP | HEI 7-6995 B2 | 1/1995 |
| JP | 9-54023 A | 2/1997 |
| JP | 3119773 | 2/2006 |

OTHER PUBLICATIONS

Office Action dated May 11, 2011 from Japanese Patent Application No. 2006-171609, together with brief summary in English language, 3 pages.

* cited by examiner

*Primary Examiner* — Jan Ludlow

(74) *Attorney, Agent, or Firm* — Kilpatrick Townsend & Stockton LLP

(57) ABSTRACT

A dispensing apparatus includes a probe that sucks or discharges a liquid; a pressure generating unit that generates a pressure necessary for the probe to suck or discharge the liquid; and a pressure measuring unit that measures the pressure generated by the pressure generating unit and applied to the probe. The apparatus also includes a setting unit that sets a correction coefficient used when correcting a physical amount based on characteristics of the dispensing apparatus using a result of the measuring by the pressure measuring unit; a storage unit that stores therein information including the correction coefficient set by the setting unit; and a correcting unit that corrects the physical amount using the correction coefficient stored in the storage unit.

12 Claims, 5 Drawing Sheets

DISPENSING APPARATUS AND AUTOMATIC ANALYZER

CROSS-REFERENCE TO RELATED APPLICATIONS

This application is a continuation of PCT international application Ser. No. PCT/JP2007/062313 filed on Jun. 19, 2007 which designates the United States, incorporated herein by reference, and which claims the benefit of priority from Japanese Patent Application No. 2006-171609, filed on Jun. 21, 2006, incorporated herein by reference.

BACKGROUND OF THE INVENTION

1. Field of the Invention

The present invention relates to a dispensing apparatus that dispenses a liquid, and an automatic analyzer that includes the dispensing apparatus and analyzes a specimen.

2. Description of the Related Art

In an automatic analyzer that analyzes components of a specimen, a dispensing apparatus is used to dispense a reagent or a specimen and a reagent into a reaction vessel.

The dispensing apparatus has a configuration in which a narrow-tube shaped probe and a syringe that generates a pressure necessary for the probe to suck or discharge a specimen and a reagent are connected to each other via a pipe, and in which the pressure generated by the syringe is transmitted to the probe via the pipe.

A technology used in the dispensing apparatus having the above configuration is known in which the pressure applied to the probe is detected with a pressure sensor, and dispensing abnormality such as a clog in the tip of the probe is detected based on the result of the detection (see, Publication of Examined Utility Model Application H2-045818). In the conventional technology, a threshold of the pressure applied to the probe is previously set to determine whether there is a clog in the probe, and a clog in the probe is detected by comparing the threshold to a value measured by the pressure sensor.

SUMMARY OF THE INVENTION

A dispensing apparatus according to an aspect of the present invention includes a probe that sucks or discharges a liquid; a pressure generating unit that generates a pressure necessary for the probe to suck or discharge the liquid; a pressure measuring unit that measures the pressure generated by the pressure generating unit and applied to the probe; a setting unit that sets a correction coefficient used when correcting a physical amount based on characteristics of the dispensing apparatus using a result of the measuring by the pressure measuring unit; a storage unit that stores therein information including the correction coefficient set by the setting unit; and a correcting unit that corrects the physical amount using the correction coefficient stored in the storage unit.

An automatic analyzer for analyzing a specimen by reacting the specimen with a reagent, the automatic analyzer comprising the dispensing apparatus according to the present invention as a specimen dispensing unit for dispensing the specimen.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
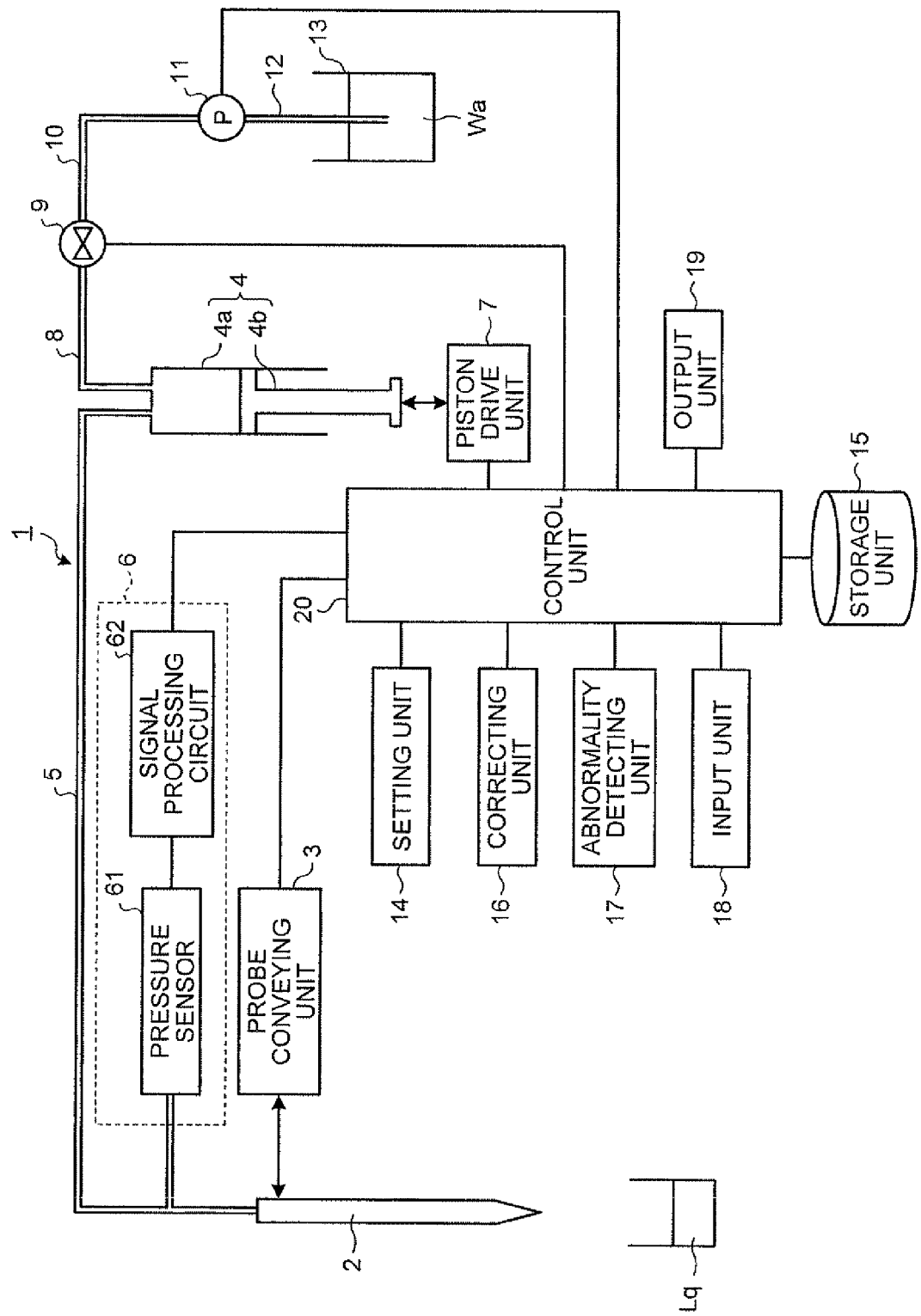
FIG. 1 is a diagram schematically showing a configuration of a dispensing apparatus according to an embodiment of the present invention.

Best modes for carrying out the present invention (hereinafter, referred to as "embodiments") are explained below with reference to the accompanying drawings. "Liquid" as used herein is intended to encompass a liquid containing a small amount of solid component. FIG. 1 is a diagram schematically showing a configuration of a dispensing apparatus according to an embodiment of the present invention. A dispensing apparatus 1 shown in FIG. 1 includes a narrow-tube shaped probe 2 that directly sucks or discharges a liquid Lq to be dispensed; a probe conveying unit 3 that conveys the probe 2 by causing the probe 2 to move up or down vertically and rotate horizontally; a syringe 4 that sucks or discharges a washing fluid Wa, which is a pressure transmitting medium that transmits a pressure to the probe 2; a tube 5 that connects the probe 2 and the syringe 4 to each other and serves as a channel for the washing fluid Wa, and a pressure measuring unit 6 that detects the pressure applied to the probe 2. The washing fluid Wa is, for example, an incompressible fluid such as ion-exchanged water or distilled water.

The syringe 4 includes a cylinder 4a and a piston 4b. A piston drive unit 7 causes the piston 4b to vertically slide in the cylinder 4a as shown in FIG. 1, so that a pressure to be transmitted to the probe 2 via the washing fluid Wa is generated. In this respect, the syringe 4 at least partly achieves the function of a pressure generating unit. The syringe 4 is also connected to a tube 8 different from the tube 5. The other end of the tube 8 is connected to an electromagnetic valve 9 that adjusts the amount of the flow of the washing fluid Wa. Another tube 10 is also connected to the electromagnetic valve 9, and the other end of the tube 10 is connected to a pump 11 that sucks or discharges the washing fluid Wa. The pump 11 is also connected to a tube 12. The other end of the tube 12 reaches a washing fluid tank 13 that contains therein the washing fluid Wa.

The pressure measuring unit 6 includes a pressure sensor 61 that is connected to the tube 5, that detects a variation in the pressure of the washing fluid Wa filled in the tube 5, and that converts the variation into an electric signal; and a signal processing circuit 62 that performs signal processing such as amplification and A/D conversion on the electric signal output from the pressure sensor 61. It is more preferable that the pressure measuring unit 6 be arranged near the probe 2. Alternatively, the pressure measuring unit 6 can be arranged between the probe 2 and the syringe 4 or near the syringe 4 depending on, for example, the sensitivity of the pressure sensor 61.

Subsequently, the configuration of the dispensing apparatus 1 is explained. The dispensing apparatus 1 includes a setting unit 14 that sets a correction coefficient α used when correcting a predetermined physical amount depending on the characteristics of the apparatus; a storage unit 15 that stores therein various types of information including the correction coefficient α set by the setting unit 14; a correcting unit 16 that reads the correction coefficient α stored in the storage unit 15 and performs a correction operation on the physical amount; an abnormality detecting unit 17 that detects dispensing abnormality using the result of the correcting by the correcting unit 16; an input unit 18 that inputs various types of information; an output unit 19 that outputs various types of information; and a control unit 20 that controls operations of the dispensing apparatus 1.

The storage unit 15 stores therein, in addition to the correction coefficient α, a reference amount to be referred by the setting unit 14 when setting the correction amount α. As an example of the reference amount according to the embodiment, is taken chronological variations of an output voltage output from a standard pressure sensor 61$s$ occurring when a standard dispensing apparatus is including the standard pressure sensor 61$s$ having a sensitivity $S_0$, and including the probe 2, the syringe 4, and a piping system that satisfies predetermined conditions dispenses a predetermined reference liquid $Lq_0$.

Figure 2:
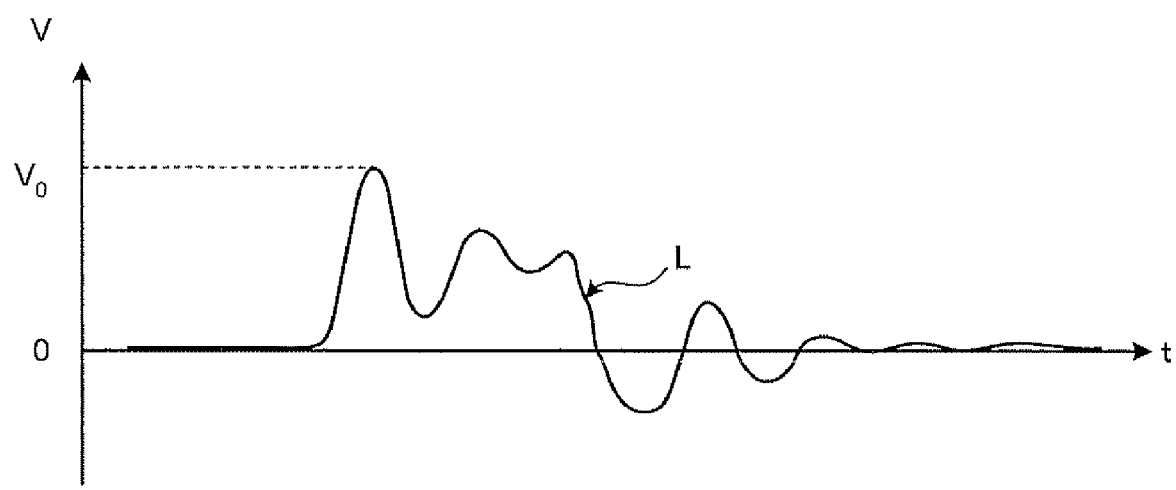
FIG. 2 is a graph schematically showing chronological variations of an output voltage of a pressure sensor occurring when a reference liquid is dispensed.

FIG. 2 is a graph schematically showing the chronological variations of the output voltage of the standard pressure sensor 61$s$ occurring when the probe 2 of the standard dispensing apparatus is normally dispenses the reference liquid $Lq_0$. In FIG. 2, the horizontal axis (t) denotes time and the vertical axis (V) denotes the output voltage of the standard pressure sensor 61$s$. Generally, a discharge pressure of the probe 2 and the output voltage of the pressure sensor 61 has a linearly relationship if errors are removed. Therefore, the discharge pressure of the probe 2 shows the chronological variations approximately same as those of the output voltage of the standard pressure sensor 61$s$, i.e., chronological variations as indicated by a curved line L shown in FIG. 2. Therefore, a maximum value $V_0$ of the output voltage of the standard pressure sensor 61$s$ corresponds to a maximum value of the discharge pressure (positive pressure) of the probe 2.

In order to determine whether dispensing abnormality occurs, the storage unit 15 stores therein, in addition to the chronological variations of the output voltage from the standard pressure sensor 61$s$, a threshold $V_{th}$ for detecting a clog in the probe 2 when dispensing the reference liquid $Lq_0$ in the standard dispensing apparatus 1$s$, and a normal range $R(Lq_0)$ of the dispensing amount of the probe 2 when dispensing the reference liquid $Lq_0$ in the standard dispensing apparatus 1$s$. The threshold $V_{th}$ and the normal range $R(Lq_0)$ can be appropriately set based on chronological variations of the discharge pressure applied to the probe 2 in a normal mode in the standard dispensing apparatus 1$s$.

It suffices that the reference liquid $Lq_0$ be a liquid having uniform viscosity. For example, as in the case of the washing fluid Wa, ion-exchanged water or distilled water can be used. It is needless to say that the configuration of the standard dispensing apparatus 1$s$ is the same as that of the dispensing apparatus 1 according to the embodiment.

The input unit 18 includes a key board and a mouse. The input unit 18 can further include a pointing device such as a trackball or a track pad, and a user interface such as an audio input microphone. The output unit 19 includes a display device such as a liquid crystal display, a plasma display, an organic EL display, or a CRT. The output unit 19 can further include an audio output speaker and a printer that prints information on a sheet and outputs the sheet.

The setting unit 14, the storage unit 15, the correcting unit 16, the abnormality detecting unit 17, and the control unit 20 are configured of a CPU, a RAM, and a ROM, etc. As the storage unit 15, an auxiliary storage device including a hard disk or an auxiliary storage device to which various types of storage media such as a CD-ROM and a flexible disk can be attached can be included.

The maximum value $V_0$ of the output voltage, the threshold $V_{th}$ for detecting a clog, the normal range $R(Lq_0)$ of the dispensing amount, which are to be stored in the storage unit 15, can be input from the input unit 18. Alternatively, they can be previously written and stored in an appropriate storage medium and read by the auxiliary storage device of the storage unit 15.

When the dispensing apparatus 1 having the above configuration performs an operation for dispensing the liquid Lq, under the control of the control unit 20, first, the electromagnetic valve 9 opens, the pump 11 sucks the washing fluid Wa, the washing fluid Wa sequentially flows into the syringe 4, the tube 5, and the probe 2, so that the syringe 4, the tube 5, and the probe 2 are filled with the washing fluid Wa. Thereafter, the electromagnetic valve 9 closes and the operation of the pump 11 is completed. Thereafter, when the probe 2 sucks or discharges the liquid Lq, under the control of the control unit 20, the piston drive unit 7 drives the syringe 4 to cause the piston 4$b$ to move, so that an appropriate suck pressure (negative pressure) or an appropriate discharge pressure (positive pressure) is generated in a tip portion of the probe 2 via the washing fluid Wa. When the liquid Lq is sucked by the tip portion of the probe 2, the liquid Lq never be mixed with the washing fluid Wa when sucking or discharging the liquid Lq, because an air layer exists between the liquid Lq and the washing fluid Wa.

Figure 3:
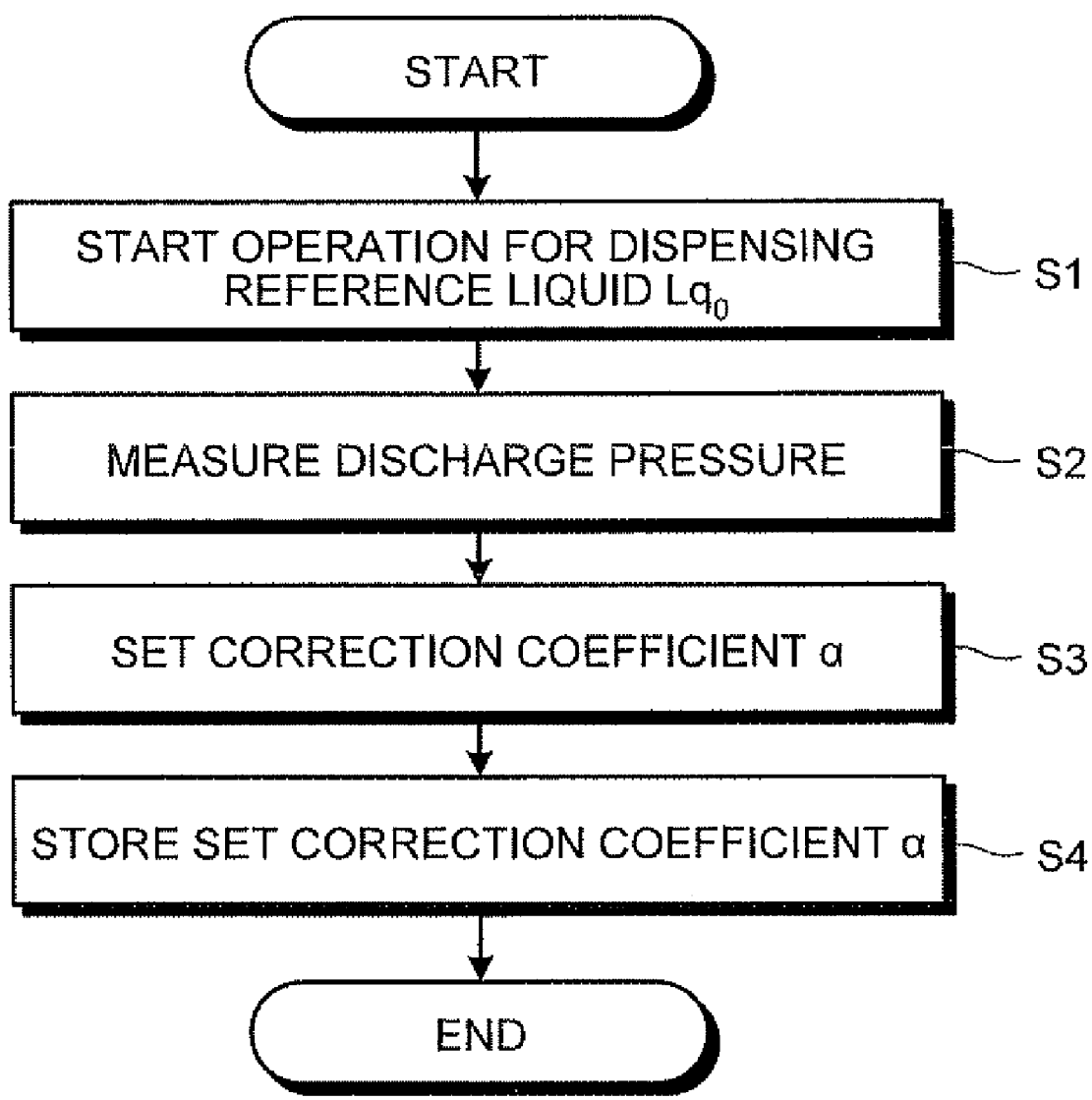
FIG. 3 is a flowchart of an outline of a correction coefficient setting process performed by the dispensing apparatus according to the embodiment of the present invention.

An outline of a process for setting the correction coefficient α in the setting unit 14 is explained with reference to the flowchart shown in FIG. 3. In the dispensing apparatus 1, the operation for dispensing the reference liquid $Lq_0$ is started (step S1). The pressure measuring unit 6 measures a discharge pressure of the probe 2 when discharging the reference liquid $Lq_0$ (step S2). The output voltage from the pressure sensor 61 corresponding to the discharge pressure measured at step S2 shows chronological variations approximately same as those indicated by the curved line L shown in FIG. 2. However, the chronological variations do not necessarily match with the curved line L. In addition, a sensitivity S of the pressure sensor 61 is not necessarily equal to the sensitivity $S_0$ of the standard pressure sensor 61$s$. Actually, it is assumed that the pressure sensor 61 used in the dispensing apparatus 1 according to the present invention has variations of about ±20% to 30% in its sensitivity. For this reason, the maximum voltage V if the output voltage output from the pressure sensor 61 measured at step S2 is not necessarily equal to the maximum value $V_0$ shown in FIG. 2.

Thereafter, the setting unit 14 sets the correction coefficient α, using the result of the measuring at step S2 (step S3). The process for setting the correction coefficient α at step S3 is described in detail below. It is known that, while the sensitivity S of the pressure sensor 61 includes variations of about ±20% to 30% as described above, a ratio V/S of the maximum value V of the output voltage of the pressure sensor 61 to the sensitivity S of the pressure sensor obtained when the liquid Lq is normally dispensed using the pressure sensor 61 (including standard pressure sensor 61$s$) having different sensitivities has sufficiently small variations compared with the variations of the sensitivity S of the pressure sensor 61. For this reason, it is assumed that the ratio V/S is a constant value regardless of the sensitivity S of the pressure sensor 61 (Assumption 1). It is also assumed that other constituents of the dispensing apparatus 1 are approximately same as those of a conventional dispensing apparatus under the same conditions.

Hereinafter, the sensitivity of the pressure sensor 61 of the dispensing apparatus 1 is denoted by $S_1$. Provided that the maximum value of the output pressure obtained when the reference liquid Lq is dispensed with the pressure sensor 61 is $V_1$, $$V_0/S_0 = V_1/S_1 \quad (1)$$

is satisfied under the assumption 1. From Equation (1), $$V_0/V_1 = S_0/S_1 \quad (2)$$

is satisfied. Equation (2) indicates that, even if the sensitivity $S_1$ is not known, an amount equivalent to the ratio of the sensitivity $S_0$ of the standard pressure sensor 61s to the sensitivity $S_1$ of the pressure sensor 61 is obtained using the value $V_0$ stored in the storage unit 15 and the maximum value $V_1$ of the output voltage of the pressure sensor 61. Therefore, by reading $V_0$ from the storage unit 15, referring to $V_0$, and obtaining the result of the measuring by the pressure measuring unit 6 at step S2, the setting unit 14 calculates the correction coefficient α as $$\alpha = V_0/V_1 \quad (3)$$

and sets the correction coefficient α. As it is clear from Equation (3), α=1 is satisfied when the sensitivity $S_1$ of the pressure sensor 61 is equal to the sensitivity $S_0$ of the pressure sensor 61 ($S_1 = S_0$).

The value of the correction coefficient α set at step S3 is stored in the storage unit 15 under the control of the control unit 20 (step S4).

The setting unit 14 can repeat the processing from step S1 to step S3 for a predetermined number of times and set, as the correction coefficient, $\alpha^{(mean)}$ obtained by averaging the values of the correction coefficient α, each of which is obtained in each processing.

Figure 4:
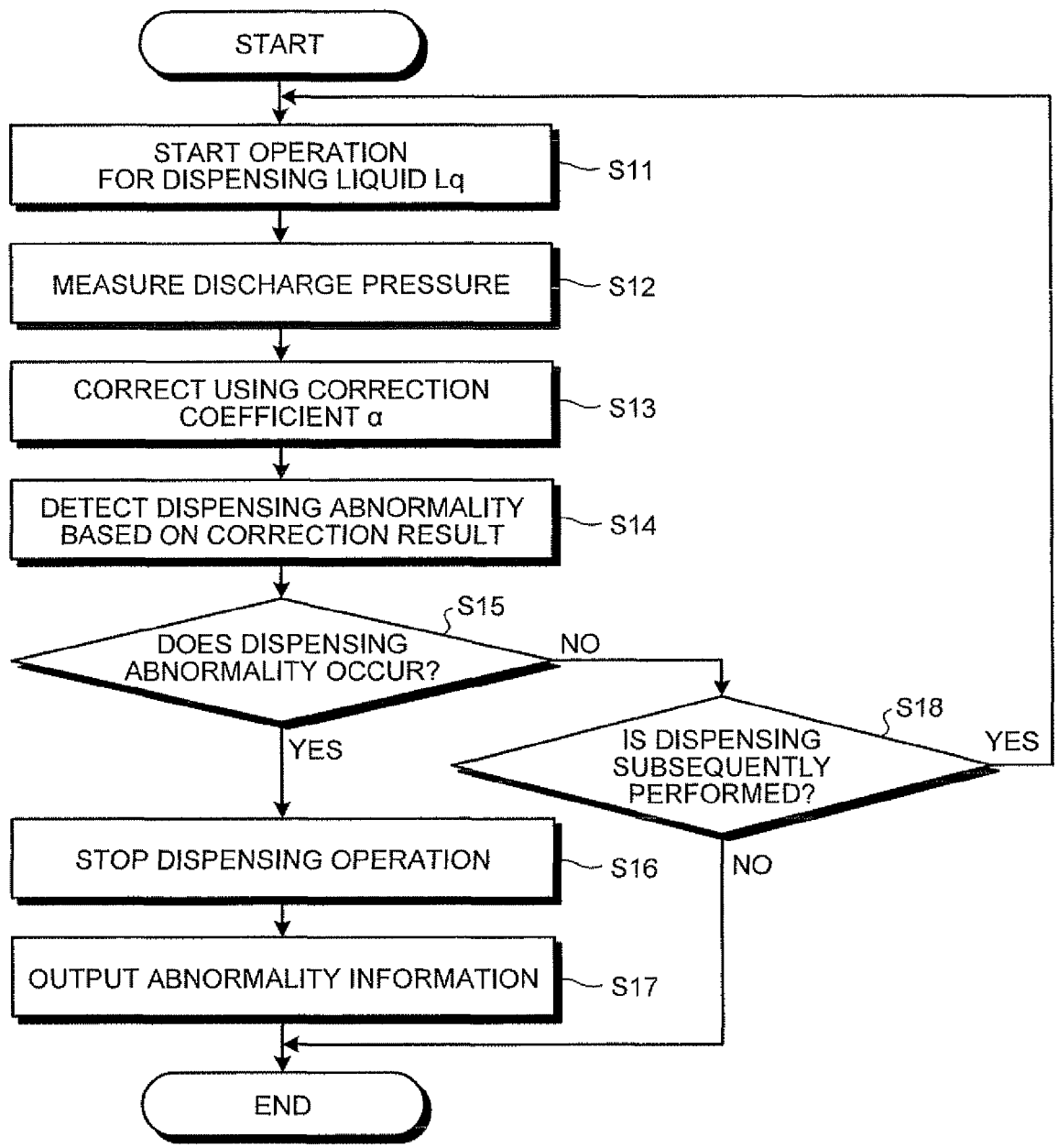
FIG. 4 is a flowchart of an outline of a dispensing abnormality detecting process performed by the dispensing apparatus according to the embodiment of the present invention.

Subsequently, an outline of a process for detecting dispensing abnormality performed by the abnormality detecting unit 17 while the liquid Lq is dispensed is explained with reference to the flowchart shown in FIG. 4. In the dispensing apparatus 1, first, the operation for dispensing the liquid Lq is started (step S11). The discharge pressure of the probe 2 generated when discharging the liquid Lq is measured (step S12).

After step S12, the correcting unit 16 corrects the output voltage V(t) of the pressure sensor 61 measured at step S2 as $$V'(t) = \alpha \times V(t) \quad (4)$$

using the read correction coefficient α (step S13). The value V'(t) obtained by the correction is the value converting the output voltage of the pressure sensor 61 to the value of the output voltage from the standard pressure sensor 61s.

Thereafter, the abnormality detecting unit 17 performs abnormality detection on the dispensing operation of the dispensing apparatus 1, using the sensor output voltage V'(t) obtained by the correction (step S14). Specifically, by comparing the sensor output voltage V'(t) to the threshold $V_{th}$ for detecting a clog, which is stored in the storage unit 15, it is determined whether there is a clog in the probe 2. At the same time, by comparing the dispensing amount of the probe 2 calculated using the sensor output voltage V'(t) to the normal range R(Lq₀) stored in the storage unit 15, it is determined whether the dispensing amount of the probe 2 is small or large.

When the abnormality detecting unit 17 detects dispensing abnormality (YES at step S15), under the control of the control unit 20, the dispensing operation is terminated (step S16) and the output unit 19 outputs abnormality information (step S17). It is preferable that the abnormality information output at step S17 contain specific contents of dispensing abnormality (for example, whether a clog exists or whether the dispensing amount is small or large).

On the other hand, when the abnormality detecting unit 17 does not detect dispensing abnormality (NO at step S15), and when there is a dispensing process to be subsequently performed (YES at step S18), the process control goes back to step S1 and the processing is repeated. On the other hand, when there is no dispensing process to be subsequently performed (NO at step S18), a series of processing are completed.

The physical amount corrected by the correcting unit 16 at step S13 can be one other than the output voltage of the pressure sensor 61. For example, the threshold $V_{th}$ for detecting a clog in the probe 2 or the normal range R(Lq₀) of the dispensing amount can be corrected. In this case, provided that a threshold for detecting a clog when the reference liquid Lq₀ is dispensed in the dispensing apparatus 1 (generally, different from the standard dispensing apparatus 1s) is $V_{th}^{(1)}$, a ratio of the threshold $V_{th}^{(1)}$ to the threshold $V_{th}$ for detecting a clog when the reference liquid Lq₀ is dispensed in the standard dispensing apparatus 1s should be equal to the ratio of the sensitivities of the pressure sensors 61 and 61s of the respective dispensing apparatuses. Therefore, $$V_{th}/V_{th}^{(1)} = S_0/S_1 = V_0/V_1 \quad (5)$$

is satisfied. The last equation depends on Equation (2) From Equation (5), the threshold $V_{th}^{(1)}$ is represented as $$V_{th}^{(1)} = (V_1/V_0) \times V_{th} = \alpha^{-1} \times V_{th} \quad (6)$$

using the known threshold $V_{th}$ of the standard dispensing apparatus 1s. The last Equation depends on Equation (3). A normal range $R^{(1)}$ (Lq₀) of the dispensing amount of the dispensing apparatus 1 can be obtained as well by performing the same correction operation as that explained above using the correction coefficient α on the normal range R(Lq₀) of the dispensing amount of the standard dispensing apparatus 1s.

As another physical amount, for example, a factor with which a signal is amplified by the signal processing circuit 62 can be corrected. Alternatively, a digital value obtained by A/D conversion by the signal processing circuit 62 can be corrected. It is needless to say, also in this case, that a correction operation can be performed using the correction coefficient α used in Equation (3).

In the dispensing apparatus 1 explained above, variations due to differences between apparatuses can be corrected by internal adjustment of the apparatus without using expensive devices as the probe 2 and the pressure sensor 61, which improves accuracy in measurement including detection of dispensing abnormality. Therefore, the manufacturing cost does not increase compared with the conventional dispensing apparatus, which is economical.

Figure 5:
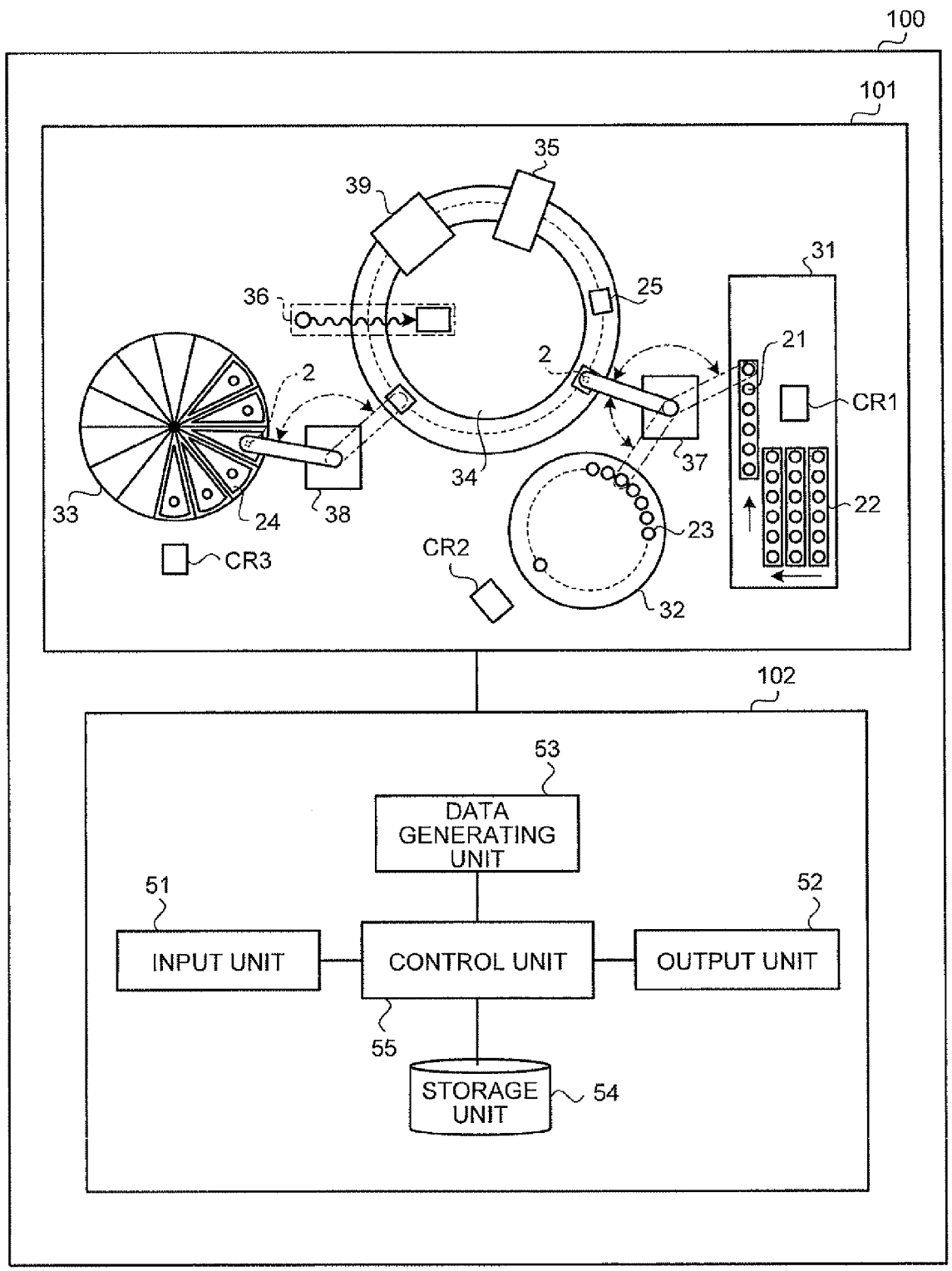
FIG. 5 is a diagram schematically showing a relevant portion of an automatic analyzer according to an embodiment of the present invention.

The dispensing apparatus 1 according to the embodiment can be applied to an automatic analyzer that analyzes components of a specimen. FIG. 5 is a diagram schematically showing a configuration of a relevant portion of an automatic analyzer according to an embodiment of the present invention. An automatic analyzer 100 shown in FIG. 5 includes a measuring system 101 that dispenses a specimen and a reagent corresponding to the liquid Lq to predetermined vessels and performs optical measurement on the liquid contained in the vessels; and a control analyzing system 102 that controls the automatic analyzer 100 including the measuring system 101 and analyzes a result of the measurement by the measuring system 101. The measuring system 101 and the control analyzing system 102 cooperate to automatically and sequentially perform biochemical analysis on components of a plurality of specimens.

First, the measuring system 101 of the automatic analyzer 100 is explained. The measuring system 101 mainly includes a specimen conveying unit 31 that houses therein a plurality of racks 22 each mounting thereon specimen vessels 21, and that sequentially conveys the racks 22; a specimen vessel holding unit 32 that holds specimen vessels 23 that stores therein various types of specimens (such as a standard specimen for generating an analytical curve, an accuracy management specimen, an urgent specimen, a STAT specimen, and a re-examination specimen) other then a normal specimen; a reagent vessel holding unit 33 that holds reagent vessels 24; a reaction vessel holding unit 34 that holds a reaction vessel 25 used for reacting the specimen and the reagent; a stirring unit 35 that stirs the liquid contained in the reaction vessel 25; and an optical measuring unit 36 that measures, for example, intensity of each wavelength component of a light having passed through the reaction vessel 25.

The measuring system 101 includes a specimen dispensing unit 37 that dispenses the specimens contained in the specimen vessel 21 on the specimen conveying unit 31 and the specimen vessel 23 on the specimen vessel holding unit 32 to the reaction vessel 25; a reagent dispensing unit 38 that dispenses the reagent contained in the reagent vessel 24 on the reagent vessel holding unit 33 into the reaction vessel 25; and a cleansing unit 39 that cleanses the reaction vessel 25. The specimen dispensing unit 37 and the reagent dispensing unit 38 have functional configurations as that of the dispensing apparatus 1 described above, and can detect the surface of the liquid contained in the reaction vessel 25.

Each of the specimen vessels 21 and 23 is attached with an information code recording medium that records therein identification information that identifies a specimen stored therein as an information code such as a barcode or a two-dimensional code (not shown). Similarly, the reagent vessel 24 is attached with an information code recording medium that records therein identification information that identifies a reagent stored there in as an information code such as a barcode or a two-dimensional code (not shown). Therefore, the measuring system 101 is provided with an information code reading unit CR1 that reads the information code attached to the specimen vessel 21; an information code reading unit CR2 that reads the information code attached to the specimen vessel 23; and an information code reading unit CR3 that reads the information code attached to the reagent vessel 24.

The specimen vessel holding unit 32, the reagent vessel holding unit 33, and the reaction vessel holding unit 34 respectively includes wheels respectively holding the specimen vessels 23, the reagent vessels 24, and the reaction vessel 25; and drive units (not shown) that are respectively attached to the center of the bottom surfaces of the wheels, and that respectively drives the wheels to rotate on vertical lines penetrating the centers as rotation axes.

The inside of each vessel holding unit is maintained at a predetermined temperature. For example, the temperature in the reagent vessel holding unit 33 is set to a temperature lower than the room temperature for preventing degradation or denaturation of the reagent. The temperature in the reaction vessel holding unit 34 is set to a temperature approximately same as the human body temperature.

The optical measuring unit 36 includes a light source that emits a white light; a spectrometry optical system that performs spectrometry on the white light having passed through the reaction vessel 25; and a light receiving device that receives the light having undergone spectrometry on a component basis and converts the light into electric signals.

Because, in many cases, two types of reagents are used for one specimen to biochemically analyze components of one specimen, the reagent vessel holding unit 33 for a first reagent and the reagent vessel holding unit 33 for a second reagent can be independently provided. In this case, it suffices that two reagent dispensing units 38 corresponding to the respective reagent vessel holding unit 33 be provided. To simultaneously stir the liquids in the reaction vessels at appropriate timing after a specimen or a reagent is dispensed, a plurality of stirring units 35 can be provided.

Because FIG. 5 focuses on schematically showing the relevant constituents, the positional relationship between the constituents is not necessarily accurate. The accurate positional relationship between the constituents is a matter of design to be determined depending on various types of conditions such as the number of the reagent vessel holding unit 33 or how the wheel of the reaction vessel holding unit 34 rotates.

Subsequently, the control analyzing system 102 of the automatic analyzer 100 is explained. The control analyzing system 102 includes an input unit 51 that receives an input of information including information necessary for analyzing a specimen and instruction signals for operating the automatic analyzer 100; an output unit 52 that outputs information about analysis on the specimen; a data generating unit 53 that generates analysis data about the specimen based on the result of the measuring by the measuring system 101; a storage unit 54 that stores therein various types of information including information about the analysis on the specimen and information about the automatic analyzer 100; and a control unit 55 that controls each function or each unit of the control analyzing system 102 and controls driving the measuring system 101.

The data generating unit 53 performs an analysis operation on the measurement result received from the optical measuring unit 36 of the measuring system 101. In the analysis operation, analysis data about each specimen is generated by calculating an absorbance of the liquid in the reaction vessel based on the measurement result transmitted from the optical measuring unit 36 and performing component amount calculation processing for quantitatively obtaining the components of the liquid in the reaction vessel 25, using various types of information including the result of calculating the absorbance, the analytical curve, and analysis parameters. The analysis data thus generated is written and stored in the storage unit 54 while being output from the output unit 52.

The storage unit 54 stores therein and manages analysis items, specimen information, reagent types, amounts of reagent and specimen to be dispensed, expiry dates of specimens and reagents, information about analytical curves used for analysis, expiry dates of the analytical curves, parameters necessary for analysis such as a reference value and an allowable value of each analysis item, and the analysis data generated by the generating unit 53.

The input unit 51, the output unit 52, the storage unit 54, and the control unit 55 have functions of the input unit 18, the output unit 19, the storage unit 15, and the control unit 20, respectively.

In the automatic analyzer 100, a liquid containing solid components, such as blood, is sometimes used as a specimen. Attachment of the solid components to the interior of the probe 2 easily leads to a clog in the probe 2. In addition, if cleansing is insufficient, an error in the dispensing amount may be caused. By applying the dispensing apparatus 1 according to the embodiment to the specimen dispensing unit 37 and the reagent dispensing unit 38, dispensing abnormality can be accurately detected regardless of a characteristic difference between apparatuses.

According to the embodiments of the present invention explained above, it possible to provide the dispensing apparatus in which, while the manufacturing cost is maintained, dispensing abnormality can be detected with high accuracy regardless of the characteristics of each apparatus, and the automatic analyzer including the dispensing apparatus, because the dispensing apparatus includes the probe that sucks or discharges a liquid; the syringe that generates a pressure necessary for the probe to suck or discharge the liquid; the pressure measuring unit that measures the pressure applied to the probe; the setting unit that sets the correction coefficient $\alpha$ used when correcting the physical amount based on the characteristics of the apparatus using the result of the measuring by the pressure measuring unit; the storage unit that stores therein the information including the correction coefficient set by the setting unit; and the correcting unit that corrects the physical amount using the correction coefficient stored in the storage unit.

The best modes for carrying out the present invention are explained in detail above. However, the present invention should not be limited to the embodiments described above. For example, the dispensing apparatus according to the present invention is preferably applied to a specimen dispensing unit of an automatic analyzer of a type in which a blood type is determined based on homogeneous reaction such as a condensation technology, or in which antigens or antibodies relating to infectious diseases are detected. In this type of automatic analyzer, after a specimen such as blood cell or blood plasma is diluted with a predetermined diluent, the specimen and a reagent are mixed and stirred using a micro plate having wells, in which a plurality of specimens can be contained in matrix, and left in the well for a predetermined reaction time. Thereafter, the specimen is analyzed by taking reaction images (aggregate images) with a high-resolution CCD camera. In this case, because a small amount of the specimen is dispensed, it is required to detect dispensing abnormality with high accuracy. For this reason, the use of the dispensing apparatus according to the present invention makes it possible to accurately detect dispensing abnormality regardless of the characteristics of each apparatus, which prevents false determination.

The dispensing apparatus according to the present invention can be also applied to an automatic analyzer that performs immunity analysis based on heterogeneous reactions. In this case, it suffices that a B/F cleansing unit that performs B/F cleansing necessary for immunity analysis using heterogeneous reactions and a photoelectron multiplying tube be provided. Except for these aspects, the configuration of the automatic analyzer is approximately same as that of the automatic analyzer 100. A configuration can be adopted in which the air can be applied to a pressure transmitting medium instead of a washing fluid and a specimen and a reagent is dispensed by adjusting the pressure by the air. Furthermore, a configuration can be adapted in which a disposable chip can be attached to the tip of the probe. When this type of automatic analyzer performs, for example, immunity analysis, a small amount of a specimen is dispensed in many cases as well. Therefore, effects same as those obtained with the above-mentioned automatic analyzer that performs analysis based on heterogeneous reactions can be obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A dispensing apparatus comprising:
   a probe that sucks or discharges a liquid;
   a pressure generating unit that generates a pressure necessary for the probe to suck or discharge the liquid;
   a pressure measuring unit that measures the pressure generated by the pressure generating unit and applied to the probe;
   a first processor, the first processor configured to set a correction coefficient used when correcting a physical amount based on characteristics of the dispensing apparatus;
   a storage unit that stores therein information including a reference pressure of a standard pressure measuring unit and the correction coefficient set by the first processor, the first processor configured to set the correction coefficient; and
   a second processor, the second processor configured to correct the physical amount using the correction coefficient stored in the storage unit, the corrected physical amount being used for detecting abnormality,
   wherein the first processor is configured to set the correction coefficient using the reference pressure stored in the storage unit and a result measured by the pressure measuring unit when sucking or discharging a reference liquid, the correction coefficient representing a difference between the pressure measuring unit and the standard pressure measuring unit.

2. The dispensing apparatus according to claim 1, wherein the first processor and the second processor comprise a central processor.

3. The dispensing apparatus according to claim 1, wherein the pressure measuring unit includes
   a pressure sensor that detects a variation in the pressure applied to the probe and converts the variation into an electric signal; and
   a signal processing circuit that performs signal processing including amplification and A/D conversion on an output of the pressure sensor.

4. The dispensing apparatus according to claim 3, wherein the physical amount includes the output of the pressure sensor.

5. The dispensing apparatus according to claim 3, wherein the physical amount includes a factor with which a signal is amplified by the signal processing circuit.

6. The dispensing apparatus according to claim 3, wherein the physical amount includes a digital value output after the A/D conversion by the signal processing circuit.

7. The dispensing apparatus according to claim 1, further comprising a third processor, the third processor configured to detect abnormalities that detects a dispensing abnormality of the dispensing apparatus by use of the physical amount corrected by the second processor, the second processor configured to correct.

8. The dispensing apparatus according to claim 7, wherein the third processor, the third processor configured to detect abnormalities determines whether there is a clog in the probe by comparing a maximum value of a discharge pressure applied to the probe with a predetermined threshold, and the third processor, the third processor configured to detect abnormalities determines whether a dispensing amount of the probe is small or large by comparing the dispensing amount with a predetermined normal range.

9. The dispensing apparatus according to claim 8, wherein the physical amount includes the threshold and the normal range.

10. The dispensing apparatus according to claim 7, wherein the first processor and second processor and the third processor comprise a central processor.

11. An automatic analyzer for analyzing a specimen by reacting the specimen with a reagent, the automatic analyzer comprising a dispensing apparatus as a specimen dispensing unit for dispensing the specimen, the dispensing apparatus including:

a probe that sucks or discharges a liquid;

a pressure generating unit that generates a pressure necessary for the probe to suck or discharge the liquid;

a pressure measuring unit that measures the pressure generated by the pressure generating unit and applied to the probe;

a first processor, the first processor configured to set a correction coefficient used when correcting a physical amount based on characteristics of the dispensing apparatus;

a storage unit that stores therein information including a reference pressure of a standard pressure measuring unit and the correction coefficient set by the first processor, the first processor configured to set the correction coefficient; and a second processor, the second processor configured to correct the physical amount using the correction coefficient stored in the storage unit, the corrected physical amount being used for detecting abnormality, wherein the first processor is configured to set the correction using the reference pressure stored in the storage unit and a result, measured by the pressure measuring unit when sucking or discharging a reference liquid, the correction coefficient representing a difference between the pressure measuring unit and the standard pressure measuring unit.

12. The dispensing apparatus according to claim 11, wherein the first processor and the second processor comprise a central processor.

* * * * *